US007271182B2

(12) United States Patent
Kamiyama et al.

(10) Patent No.: US 7,271,182 B2
(45) Date of Patent: Sep. 18, 2007

(54) SALTS OF BENZIMIDAZOLE COMPOUND AND USE THEREOF

(75) Inventors: Keiji Kamiyama, Ibaraki (JP); Hideo Hashimoto, Kobe (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/343,142

(22) PCT Filed: Aug. 3, 2001

(86) PCT No.: PCT/JP01/06686

§ 371 (c)(1),
(2), (4) Date: Jan. 28, 2003

(87) PCT Pub. No.: WO02/12225

PCT Pub. Date: Feb. 14, 2002

(65) Prior Publication Data

US 2003/0181487 A1 Sep. 25, 2003

(30) Foreign Application Priority Data

Aug. 4, 2000 (JP) .............................. 2000-236651

(51) Int. Cl.
*A61K 31/4439* (2006.01)
*C07D 401/12* (2006.01)
(52) U.S. Cl. .................................. 514/338; 546/273.7
(58) Field of Classification Search ................ 514/338; 546/273.7
See application file for complete search history.

(56) References Cited

U.S. PATENT DOCUMENTS 6,002,011 A * 12/1999 Kato et al. ................ 546/273.7
6,124,464 A *  9/2000 Hogberg et al. .......... 546/273.7
6,462,058 B1* 10/2002 Fujishima et al. .......... 514/338

FOREIGN PATENT DOCUMENTS

| EP | 1 277 752 |   | 1/2003 |
| JP | 61-50978 |   | 3/1986 |
| US | 2003/0153766 | * | 8/2003 |
| WO | WO92/08716 |   | 5/1992 |
| WO | WO94/27988 |   | 12/1994 |
| WO | WO96/02535 |   | 2/1996 |
| WO | WO97/41114 |   | 11/1997 |
| WO | WO99/27917 |   | 6/1999 |
| WO | 99/38513 | * | 8/1999 |
| WO | WO99/38513 |   | 8/1999 |
| WO | WO 00/78745 |   | 12/2000 |
| WO | WO 01/14366 |   | 3/2001 |
| WO | WO 01/87874 |   | 11/2001 |

OTHER PUBLICATIONS

Kotar et a., Eur. J of Pharm, Sci., 4 (1996) pp. S182.*

Brittain, Polymorphism in Pharmaceutical Sciences, NY: Marcel Dekker, Inc. (1999) pp. 126-358.*
Chemical & Engineering News, Feb. 2003, pp. 32-35.*
US Pharmacopia, 1995, pp. 1843-1844.*
Concise Encyclopedia Chemistry, pp. 872-873 (1993).*
Buck, G., et al., "Relation of *Campylobacter pylordis* to Gastritis and Peptic Ulcer", The Journal of Infectious Diseases, (1986), vol. 153, No. 4, pp. 664-669.
Hopkins, R., et al., "Relationship Between *Helicobacter pylori* Eradication and Reduced Duodenal and Gastric Ulcer Recurrence: A Review", Gastroenterology, (1996), vol. 110, No. 4, pp. 1244-1252.
Laine, L., et al., "Has the Impact of *Helicobacter pylori* Therapy on Ulcer Recurrence in the United States been Overstated?" The American Journal of Gastroeneterology, (1998), vol. 93, No. 9, pp. 1409-1415.
Katoh, M., et al., "Clinical Efficacy of Lansoprazole in Eradication of *Helicobacter pylori*", J. Clin Gastroenterol, (1995), vol. 20, Suppl. 2, pp. S112-S114.
Sugiyama, T., et al., "Lansoprazole versus Lansoprazole plus Amoxicillin treatment for Eradication of *Helicobacter pylori* in Patients with Gastric Ulcer", J. Clin Gastroenterol, (1995), vol. 20, Suppl. 2, pp. S104-S106.
Takimoto, T., et al., "Efficacy of Lansoprazole in Eradication of *Helicobacter pylori*", J. Clin Gastroenterol, (1995), vol. 20, Suppl. 2, pp. S121-S124.
Ogoshi, K., et al., "Peptic Ulcer Therapy with Lansoprazole and *Helicobacter pylori* Eradication", J. Clin Gastroenterol, (1995), vol. 20, Suppl. 2, pp. S97-S99.
Iwahi, T., et al., "Lansoprazole, a Novel Benzimidazole Proton Pump Inhibitor, and its Related Compounds have Selective Activity against *Helicobacter pylori*", Antimicrobial Agents and Chemotherapy, (1991), vol. 35, No. 3, pp. 490-496.
Nakao, M., et al., "Antibacterial Properties of Lansoprazole alone and in Combination with Antimicrobial Agents against *Helicobacter pylori*", Eur. J. Clin. Microbiol. Infect. Dis., (1995), vol. 14, No. 5, pp. 391-399.
Alarcon, T., et al., "In Vitro Activity of Ebrotidine, Ranitidine, Omeprazole, Lansoprazole, and Bismuth Citrate against Clinical Isolates of *Helicobacter pylori*", Eur. J. Clin. Microbiol. Infect. Dis., (1998), vol. 17, pp. 275-277.
Vogt, K., et al., "Bactericidal Activity of Lansoprazole and Omeprazole against *Helicobacter pylori* in vitro", Arzneim.-Forsch./Drug Res. 48, (1998), No. 6, pp. 694-697.
Nakao, M., et al., "Growth Inhibitory and Bactericidal Activities of Lansoprazole Compared with those of Omeprazole and Pantoprazole against *Helicobacter pylori*", Helicobacter, (1998), vol. 3, No. 1, pp. 21-27.
Malfertheiner, P., et al., "Current Concepts in the Management of *Helicobacter pylori* Infection-The Maastricht Feb. 2000 Consensus Report", Aliment Pharmacol Ther, (2002), vol. 16, pp. 167-180.
PREVACID Package Insert, pp. 1-32.

* cited by examiner

*Primary Examiner*—Patricia L. Morris
(74) *Attorney, Agent, or Firm*—Hamre, Schumann, Mueller & Larson, P.C.

(57) ABSTRACT

A sodium salt, magnesium salt, lithium salt, potassium salt, calcium salt or barium salt of (R)-2-[[[3-methyl-4-(2,2,2-trifluoroethoxy)-2-pyridinyl]methyl]sulfinyl]-1H-benzimidazole, and a pharmaceutical composition comprising the salt. The novel salt is useful as an excellent antiulcer agent.

10 Claims, 4 Drawing Sheets

SALTS OF BENZIMIDAZOLE COMPOUND AND USE THEREOF

This application is the National Phase filing of International Patent Application No. PCT/JP01/06686, filed 03 Aug. 2001.

TECHNICAL FIELD

The present invention relates to a salt of a benzimidazole compound having an excellent pharmaceutical activity (e.g., an antiulcer action) and its application.

BACKGROUND ART

2-[[[3-methyl-4-(2,2,2-trifluoroethoxy)-2-pyridinyl]methyl]sulfinyl]-1H-benzimidazole or a salt thereof having an antiulcer action is reported in Japanese Patent Application Laid-Open No. 50978/1986 (JP-61-50978A) and so on.

WO 94/27988 (Japanese Patent Application Laid-Open No. 509499/1995 (JP-7-509499A)) discloses, as optically pure compounds, sodium, magnesium, lithium, potassium and calcium salts of (+)-methoxy-2-[[(4-methoxy-3,5-dimethyl-2-pyridinyl)methyl]sulfinyl]-1H-benzimidazole (omeprazole) which are optically pure.

WO 99/38513 discloses a method of treating ulcers, etc. which comprises administering an optically pure (R)-lansoprazole or a pharmaceutically acceptable salt thereof. However, this literature practically fails to disclose how to produce the salt.

WO 92/8716 discloses a pyridylmethylsulfiniyl-1H-benzimidazol compound which is enantiomerically pure, or a salt thereof and a process for producing the same.

WO96/2535 (U.S. Pat. No. 5,948,789, Japanese Patent Application Laid-Open No. 504290/1998 (JP-10-504290A)) discloses a production process which comprises subjecting a thio compound to an oxidation reaction for forming an optically active sulfoxide compound such as omeprazole and, if desired, converting the sulfoxide compound into a salt thereof by a conventional process.

The pyridylmethylsulfinyl-1H-benzimidazole compounds (e.g., omeprazole, lansoprazole) described in these literatures are relatively inferior in stability. Moreover, it is difficult to provide an optically active lansoprazole with high purity. However, these literatures fail to disclose a process for improving a stability and a purity of an optically active lansoprazole.

It is, therefore, an object of the present invention to provide an optically active lansoprazole having a high stability and its application (e.g., a pharmaceutical composition such as an antiulcer agent).

Another object of the present invention is to provide an optically active lansoprazole having a high-purity and its application.

Still another object of the present invention is to provide an optically active lansoprazole which has an improved stability and is excellent in solubility and absorbability and its application.

DISCLOSURE OF INVENTION

The inventors of the present invention did intensive research, and finally found that specific metal salts (especially, salts in the form of crystal) of (R)-2-[[[3-methyl-4-(2,2,2-trifluoroethoxy)-2-pyridinyl]methyl]sulfinyl]-1H-benzimidazole can be synthesized for the first time and that such a salt unexpectedly has an excellent stability as a solid and an antiulcer action, and satisfactorily serves as a pharmaceutical. The present invention was accomplished based on the above findings.

That is, the present invention relates to a sodium salt, a lithium salt, a potassium salt, a magnesium salt, a calcium salt, or a barium salt of (R)-2-[[[3-methyl-4-(2,2,2-trifluoroethoxy)-2-pyridinyl]methyl]sulfinyl]-1H-benzimidazole. The salt may be a crystal. For example, the salt of the present invention may be a sodium salt (in particular a crystal) of (R)-2-[[[3-methyl-4-(2,2,2-trifluoroethoxy)-2-pyridinyl]methyl]sulfinyl]-1H-benzimidazole, a potassium salt (in particular a crystal) of (R)-2-[[[3-methyl-4-(2,2,2-trifluoroethoxy)-2-pyridinyl]methyl]sulfinyl]-1H-benzimidazole, and the like. Further, the salt of the present invention may be solvated. In the salt in the form of crystal, the X-ray diffraction spectrum of the crystal may, for example, have the following diffraction peaks:

(i) 15.02, 7.53, 7.05, 5.53, 4.17, 3.96, 3.42, 3.33 Å, (ii) 16.00, 12.65, 7.98, 7.51, 6.35, 5.09, 4.99, 4.92, 4.82, 4.21 Å, (iii) 8.89, 8.47, 5.64, 5.24, 4.84, 4.23, 4.20, 4.09, 3.60, 3.36 Å, or (iv) 16.35, 8.17, 6.81, 5.78, 4.93, 4.50, 4.25, 4.08, 3.65, 3.36, 3.02 Å.

According to the process of the present invention, a metal salt of (R)-2-[[[3-methyl-4-(2,2,2-trifluoroethoxy)-2-pyridinyl]methyl]sulfinyl]-1H-benzimidazole is produced by reacting (R)-2-[[[3-methyl-4-(2,2,2-trifluoroethoxy)-2-pyridinyl]methyl]sulfinyl]-1H-benzimidazole with a compound of a metal selected from the group consisting of sodium, lithium, potassium, magnesium, calcium and barium. In the process, a metal salt of (R)-2-[[[3-methyl-4-(2,2,2-trifluoroethoxy)-2-pyridinyl]methyl]sulfinyl]-1H-benzimidazole in a crystalline form can be obtained by subjecting the metal salt of (R)-2-[[[3-methyl-4-(2,2,2-trifluoroethoxy)-2-pyridinyl]methyl]sulfinyl]-1H-benzimidazole to crystallization.

The present invention further discloses a pharmaceutical composition comprising the above-mentioned salt. The pharmaceutical composition is utilized as a prophylactic or therapeutic agent for digestive ulcer, gastritis, reflux esophagitis, NUD (Non-Ulcer Dyspepsia), gastric cancer, gastric MALT lymphoma, upper gastrointestinal hemorrhage, ulcer caused by a nonsteroidal anti-inflammatory agent, hyperacidity and ulcer due to postoperative stress, or disease due to *Helicobacter pylori*.

The present invention furthermore discloses a method for preventing or treating digestive ulcer, gastritis, reflux esophagitis, NUD (Non-Ulcer Dyspepsia), gastric cancer, gastric MALT lymphoma, upper gastrointestinal hemorrhage, ulcer caused by a nonsteroidal anti-inflammatory agent, hyperacidity and ulcer due to postoperative stress, or disease due to *Helicobacter pylori*, which comprises administering the above-mentioned salt to human being; and discloses use of the above-mentioned salt for manufacturing a pharmaceutical composition.

Incidentally, in the specification, "sodium, lithium and potassium" and metal compounds thereof are sometimes referred to as "alkali metals" and "alkali metal compounds", respectively. Moreover, "magnesium, calcium, and barium" and metal compounds thereof are sometimes referred to as "alkaline earth metals" and "alkaline earth metal compounds", respectively.

BEST MODE FOR CARRYING OUT THE INVENTION

Figure 1:
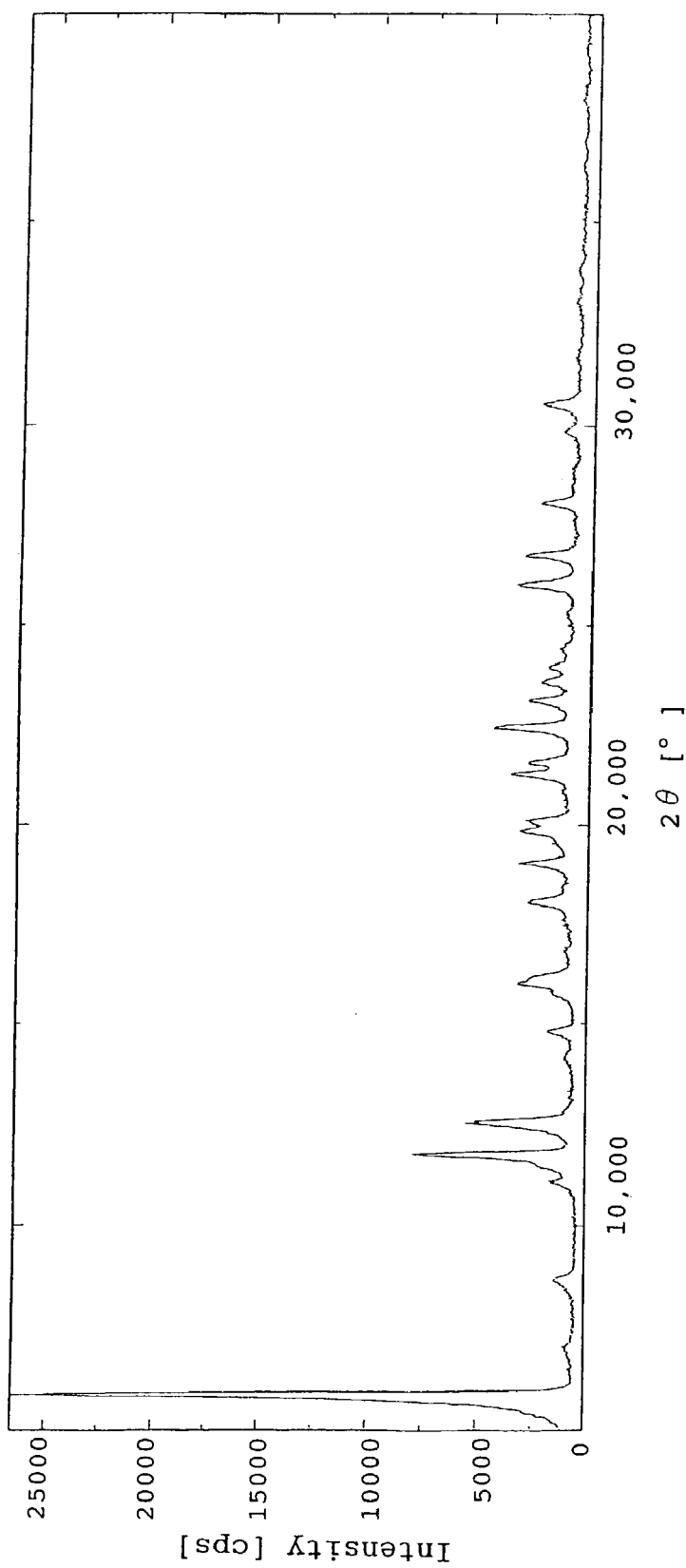
FIG. 1 is the X-ray powder diffraction analysis chart of the crystal of Example 1.

The features of the present invention reside in that 2-[[[3-methyl-4-(2,2,2-trifluoroethoxy)-2-pyridinyl]methyl]sulfinyl]-1H-benzimidazole (hereinafter, sometimes referred to as simply "lansoprazole") is an optically active (R)-form, and that (R)-lansoprazole forms a salt with a specific metal.

The sodium salt, magnesium salt, lithium salt, potassium salt, calcium salt, or barium salt of (R)-2-[[[3-methyl-4-(2,2,2-trifluoroethoxy)-2-pyridinyl]methyl]sulfinyl]-1H-benzimidazole of the present invention (hereinafter, sometimes referred to simply as "the salt of the present invention") is optically pure, and the optical purity of (R)-enantiomer is, for example, not less than 90% of enatiomer excess (e.e.), preferably not less than 95% of enatiomer excess, and more preferably not less than 99% of enatiomer excess.

The form of the salt of the present invention is not particularly limited and may be an oil, a non-crystal, or a crystal. The preferred salt form is a crystal. The crystal is identified by diffraction peaks of the X-ray diffraction spectrum. As the salt of a crystal form, there may be mentioned a sodium salt, a potassium salt and the like. Concretely, as the salt of a crystal form, there may be mentioned (i) crystal of a sodium salt of which the X-ray powder diffraction analysis pattern has characteristic peaks at lattice spacings (d) of 15.02, 7.53, 7.05, 5.53, 4.17, 3.96, 3.42, 3.33 Å, (ii) crystal of a sodium salt solvated with isopropyl alcohol, of which the X-ray powder diffraction analysis pattern has characteristic peaks at lattice spacings (d) of 16.00, 12.65, 7.98, 7.51, 6.35, 5.09, 4.99, 4.92, 4.82, 4.21 Å, (iii) crystal of a monohydrate of a sodium salt of which the X-ray powder diffraction analysis pattern has characteristic peaks at lattice spacings (d) of 8.89, 8.47, 5.64, 5.24, 4.84, 4.23, 4.20, 4.09, 3.60, 3.36 Å, (iv) crystal of a potassium salt of which the X-ray powder diffraction analysis pattern has characteristic peaks at lattice spacings (d) of 16.35, 8.17, 6.81, 5.78, 4.93, 4.50, 4.25, 4.08, 3.65, 3.36, 3.02 Å.

The salt of the present invention may be a solvate with a solvent (water, organic solvents), or may be a non-solvate. That is, the salt of the present invention may be a hydrate or not (or may be a non-hydrate).

The "hydrate" includes 0.5 hydrate to 5.0 hydrate. Among others, 0.5 hydrate to 3.0 hydrate, for example, 0.5 hydrate, 1.0 hydrate, 1.5 hydrate and 2.0 hydrate are preferred.

The salt of the present invention may contain a low-toxic or non-toxic solvent, and may be solvated with a solvent as mentioned above. The "solvent" includes, for example, alcohols [e.g., $C_{1-4}$alkylalcohols such as methanol, ethanol, 1-propanol and 2-propanol (isopropyl alcohol), benzyl alcohol]. Among them, ethanol and 2-propanol are preferred.

The content of the "solvent" is about 0.5 to 5.0 mol, preferably about 0.5 to 2 mol (e.g., about 0.5 to 1.0 mol) and more preferably about 1.0 mol relative to 1 mol of the salt of the present invention.

The salt of the present invention can be prepared by per se known methods, for example, the methods described in WO 94/27988 or analogous methods thereto. For example, the salt of the present invention can be obtained by reacting (R)-2-[[[3-methyl-4-(2,2,2-trifluoroethoxy)-2-pyridinyl]methyl]sulfinyl]-1H-benzimidazole with a compound of a metal selected from the group consisting of sodium, lithium, potassium, magnesium, calcium and barium. As the metal compound, there may be mentioned, metal hydroxides, metal carbonates, metal hydrogencarbonates, metal alkoxides, metal amides and the like. The preferred metal compound includes metal hydroxides (e.g., sodium hydroxide, potassium hydroxide, magnesium hydroxide), metal alkoxides (e.g., metal $C_{1-4}$alkoxides), and metal amides (e.g., sodium amide, potassium amide) These metal compounds can be used singly or in combination. More concretely, the salt of the present invention can be prepared by the following reactions 1 to 3.

(Reaction 1)

The sodium salt, magnesium salt, lithium salt, potassium salt, calcium salt, or barium salt of (R)-2-[[[3-methyl-4-(2,2,2-trifluoroethoxy)-2-pyridinyl]methyl]sulfinyl]-1H-benzimidazole is obtained by reacting (R)-2-[[[3-methyl-4-(2,2,2-trifluoroethoxy)-2-pyridinyl]methyl]sulfinyl]-1H-benzimidazole with a metal hydroxide (e.g., sodium hydroxide, magnesium hydroxide, lithium hydroxide, potassium hydroxide, calcium hydroxide, barium hydroxide), a metal alkoxide (e.g., a metal $C_{1-4}$alkoxide such as sodium ethoxide, sodium methoxide, potassium ethoxide, potassium methoxide, magnesium ethoxide), or a metal amide (e.g., sodium amide, potassium amide).

The amount of the "metal hydroxide, metal alkoxide, or metal amide" is 0.1 mol to large excess mol, and preferably 0.5 to 2.0 mol (especially, 0.8 to 1.5 mol) relative to 1 mol of (R)-2-[[[3-methyl-4-(2,2,2-trifluoroethoxy)-2-pyridinyl]methyl]sulfinyl]-1H-benzimidazole. The amount of the "metal hydroxide, metal alkoxide, or metal amide" is usually about 0.5 to 2 equivalents, preferably about 0.7 to 1.5 equivalents, and more preferably about 0.8 to 1.2 equivalents relative to 1 mol of (R)-2-[[[3-methyl-4-(2,2,2-trifluoroethoxy)-2-pyridinyl]methyl]sulfinyl]-1H-benzimidazole.

This reaction is usually carried out in the absence of a solvent, or in the presence of an inert solvent. As the "inert solvent", there may be used, for example, water, alcohols (e.g., methanol, ethanol, 1-propanol, 2-propanol, butanol), ketones (e.g., acetone, methyl ethyl ketone), nitriles (e.g., acetonitrile, propionitrile), amides (e.g., formamide, N,N-dimethylformamide, N,N-dimethylacetamide), ethers (e.g., diethyl ether, tert-butyl methyl ether, diisopropyl ether, dioxane, tetrahydrofuran), esters (e.g., ethyl formate, ethyl acetate), halogenated hydrocarbons (e.g., dichloromethane, chloroform, 1,2-dichloroethane), hydrocarbons (e.g., n-hexane, cyclohexane, benzene, toluene), sulfoxides (e.g., dimethylsulfoxide), polar solvents (e.g., sulfolane, hexamethylphosphoramide) and the mixed solvents of two kinds or more thereof. Among them, water and a mixed solvent of water and the alcohol (e.g., a mixed solvent of water and methanol, a mixed solvent of water and ethanol, or a mixed solvent of water and 2-propanol) are preferred. The "inert solvent" is usually used in an amount of 1 to 100-times by weight, and preferably about 2 to 50-times by weight relative to (R)-2-[[[3-methyl-4-(2,2,2-trifluoroethoxy)-2-pyridinyl]methyl]sulfinyl]-1H-benzimidazole.

The reaction temperature is usually about −10 to 80° C., preferably about 0 to 50° C., and more preferably about 0 to 30° C. The reaction time is usually about 1 minute to 6 hours, preferably about 5 minutes to 3 hours, and more preferably about 15 minutes to 1 hour.

Thus obtained salt can be separated and purified from a reaction mixture by per se known separation means (e.g., concentration, concentration under a reduced pressure, solvent extraction, crystallization, recrystallization, redistribution, chromatography).

(Reaction 2)

The alkali metal salt (sodium, lithium or potassium salt) of (R)-2-[[[3-methyl-4-(2,2,2-trifluoroethoxy)-2-pyridinyl]methyl]sulfinyl]-1H-benzimidazole obtained by a method described above may be converted to an alkaline earth metal salt (magnesium, calcium, or barium salt) of (R)-2-[[[3-methyl-4-(2,2,2-trifluoroethoxy)-2-pyridinyl]methyl]sulfinyl]-1H-benzimidazole by reacting the alkali metal salt with an alkaline earth metal compound (a chloride or a sulfate such as magnesium chloride, magnesium sulfate, calcium chloride or barium chloride).

The amount of the alkaline earth metal compound "magnesium chloride, magnesium sulfate, calcium chloride, barium chloride and the like" is −0.1 mol to large excess mol, and preferably 0.5 to 2.0 mol relative to 1 mol of the alkali metal salt (sodium, lithium or potassium salt) of (R)-2-[[[3-methyl-4-(2,2,2-trifluoroethoxy)-2-pyridinyl]methyl]sulfinyl]-1H-benzimidazole. The amount of the alkaline earth metal compound is usually about 0.5 to 2 equivalents, preferably about 0.7 to 1.5 equivalents, and more preferably about 0.8 to 1.2 equivalents relative to 1 mol of the alkali metal salt of (R)-2-[[[3-methyl-4-(2,2,2-trifluoroethoxy)-2-pyridinyl]methyl]sulfinyl]-1H-benzimidazole.

This reaction is usually carried out in the presence of an inert solvent. As the "inert solvent", there may be used, for example, water, alcohols (e.g., methanol, ethanol, 1-propanol, 2-propanol, butanol), ketones (e.g., acetone, methyl ethyl ketone), nitrites (e.g., acetonitrile, propionitrile), amides (e.g., formamide, N,N-dimethylformamide, N,N-dimethylacetamide), ethers (e.g., diethyl ether, tert-butyl methyl ether, diisopropyl ether, dioxane, tetrahydrofuran), sulfoxides (e.g., dimethylsulfoxide), polar solvents (e.g., sulfolane, hexamethylphosphoramide) and the mixed solvents of two kinds or more thereof. Among others, water, a mixed solvent of water and the alcohol (e.g., a mixed solvent of water and ethanol, or a mixed solvent of water and 2-propanol) are preferred.

The "inert solvent" is usually employed in an amount of 1 to 100-times by weight, and preferably 2 to 50-times by weight relative to the alkali metal salt (sodium, lithium or potassium salt) of (R)-2-[[[3-methyl-4-(2,2,2-trifluoroethoxy)-2-pyridinyl]methyl]sulfinyl]-1H-benzimidazole.

The reaction temperature is usually −10 to 80° C., preferably 0 to 50° C. (e.g., 10 to 50° C.), and more preferably 15 to 30° C. The reaction time is usually about 1 minute to 6 hours, preferably about 5 minutes to 3 hours, and more preferably about 15 minutes to 1 hour.

The salt obtained in the foregoing manner can be separated and purified from a reaction mixture by per se known separation means (e.g., concentration, concentration under a reduced pressure, solvent extraction, crystallization, recrystallization, redistribution, chromatography).

(Reaction 3)

An alkaline earth metal salt (magnesium, calcium, or barium salt) of (R)-2-[[[3-methyl-4-(2,2,2-trifluoroethoxy)-2-pyridinyl]methyl]sulfinyl]-1H-benzimidazole can be obtained by treating (R)-2-[[[3-methyl-4-(2,2,2-trifluoroethoxy)-2-pyridinyl]methyl]sulfinyl]-1H-benzimidazole with an amine or ammonia, and reacting the treated product with an alkaline earth metal compound (a chloride or a sulfate such as magnesium chloride, magnesium sulfate, calcium chloride or barium chloride).

As the amine, there may be mentioned alkylamines (e.g., monoC$_{1-6}$alkylamines such as ethylamine, propylamine, and isopropylamine, diC$_{1-6}$alkylamines such as diethylamine, dipropylamine and diisopropylamine, triC$_{1-6}$alkylamines such as triethylamine, tripropylamine and diisopropylethylamine), cycloalkylamines (e.g., C$_{3-8}$cycloalkylamines such as cyclohexylamine), arylamines (e.g., aniline, N,N-dimethylaniline), aralkylamines (e.g., benzylamine), heterocyclic amines (e.g., pyridine, morpholine) and the like.

The amount of the "amine or ammonia" is 0.1 mol to large excess mol, and preferably 0.5 to 2.0 mol (e.g., 0.7 to 1.5 mol) relative to 1 mol of (R)-2-[[[3-methyl-4-(2,2,2-trifluoroethoxy)-2-pyridinyl]methyl]sulfinyl]-1H-benzimidazole.

This treatment reaction with amine or ammonia is usually carried out in the presence of an inert solvent. As the "inert solvent", there may be used, for example, water, alcohols (e.g., methanol, ethanol, 1-propanol, 2-propanol, butanol), ketones (e.g., acetone, methyl ethyl ketone), nitrites (e.g., acetonitrile, propionitrile), amides (e.g., formamide, N,N-dimethylformamide, N,N-dimethylacetamide), ethers (e.g., diethyl ether, tert-butyl methyl ether, diisopropyl ether, dioxane, tetrahydrofuran), sulfoxides (e.g., dimethylsulfoxide), polar solvents (e.g., sulfolane, hexamethylphosphoramide) and the mixed solvents of two kinds or more thereof.

The reaction temperature is usually −10 to 80° C., preferably 0 to 50° C., and more preferably 0 to 30° C. The reaction time is usually about 1 minute to 6 hours, preferably about 5 minutes to 3 hours, more preferably about 15 minutes to 1 hour.

After the treatment with amine or ammonia, the reaction with an alkaline earth metal compound (e.g., magnesium chloride, magnesium sulfate, calcium chloride or barium chloride) may be carried out in the similar manner to the above (reaction 2).

The salt obtained by the above-mentioned way can be separated and purified by per se known separation means (e.g., concentration, concentration under a reduced pressure, solvent extraction, crystallization, recrystallization, redistribution, chromatography) from the reaction mixture.

(R)-2-[[[3-methyl-4-(2,2,2-trifluoroethoxy)-2-pyridinyl]methyl]sulfinyl]-1H-benzimidazole can be prepared, for example, by subjecting 2-[[[3-methyl-4-(2,2,2-trifluoroethoxy)-2-pyridinyl]methyl]sulfinyl]-1H-benzimidazole or a salt thereof to an optical resolution or by subjecting 2-[[[3-methyl-4-(2,2,2-trifluoroethoxy)-2-pyridinyl]methyl]thio]-1H-benzimidazole to an asymmetric oxidation. Incidentally, the racemic body can be prepared by known methods, for example, methods described in EP 174726 (Japanese Patent Application Laid-Open No. 50978/1986 (JP-61-50978A)) and EP 302720, or analogous methods thereto.

Methods of optical resolution includes per se known methods, for example, a fractional recrystallization method, a chiral column method, a diastereomer method, and a method with the use of a microorganism or an enzyme and so forth. Asymmetric oxidation may include per se known methods.

The "fractional recrystallization method" includes a method in which a salt of a racemate with an optically active compound [e.g., (+)-mandelic acid, (−)-mandelic acid, (+)-tartaric acid, (−)-tartaric acid, (+)-1-phenethylamine, 1-(1-naphthyl)ethylamine, 1-(2-naphthyl)ethylamine, (−)-1-phenethylamine, cinchonine, quinidine, (−)-cinchonidine, brucine, etc.] is formed, the salt is separated by fractional recrystallization etc., and, if desired, subjected to a neutralization step, to give a free optical isomer.

The "chiral column method" includes a method in which a racemate or a salt thereof is applied to a column for an optical isomer separation (chiral column). In the case of liquid chromatography, for example, optical isomers are separated by adding a racemate to a chiral column such as ENANTIO-OVM (produced by Tosoh Corporation) or CHIRAL series (produced by Daicel Chemical Industries, Ltd.), and developing the racemate in water, a buffer (e.g., phosphate buffer), an organic solvent (e.g., hexane, ethanol, methanol, isopropanol, acetonitrile, trifluoroacetic acid, diethylamine, triethylamine, etc.), or a solvent mixture thereof. In the case of gas chromatography, for example, a chiral column such as CP-Chirasil-DeX CB (produced by GL Science Inc.) is used for separating optical isomers.

The "diastereomer method" includes a method in which a racemate and an optically active reagent are reacted (preferably, an optically active reagent is reacted to the 1-position of the benzimidazole group) to give a diastereomer mixture, then the mixture is subjected to an conventional separation mean (e.g., fractional recrystallization, chromatography, etc.) to form one diastereomer, and the diastereomer is subjected to a chemical reaction (e.g., acid hydrolysis reaction, basic hydrolysis reaction, hydrogenolysis reaction, etc.) to separate the optically active reagent moiety from the reaction product, thereby the desired optical isomer is obtained. The "optically active reagent" includes, for example, optically active organic acids such as MTPA [α-methoxy-α-(trifluoromethyl)phenylacetic acid] and (−)-menthoxyacetic acid; and optically active alkoxymethyl halides such as (1R-endo)-2-(chloromethoxy)-1,3,3-trimethylbicyclo[2.2.1]heptane, etc.

By subjecting thus obtained salt to a crystallization, the metal salt of (R)-lansoprazole in the form of crystal can be obtained. The crystallization method includes per se known methods, for example, a crystallization from a solution, a crystallization from a vapor, and a crystallization from a molten form.

Methods of the "crystallization from a solution" include, for example, a concentration method, a slow cooling method, a reaction method (diffusion method, electrolysis method), a hydrothermal growth method, a fusing agent method, and so forth. Solvents to be used include, for example, aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethylsulfoxide, etc.), acid amides (e.g., N,N-dimethylformamide, N,N-dimethylacetoamide, etc.), esters (e.g., methyl acetate, ethyl acetate, etc.), alcohols (e.g., methanol, ethanol, isopropyl alcohol, butanol, etc.), water, and so forth. These solvents may be used singly or as a mixture of two or more kinds in appropriate ratios (e.g., 1:1 to 1:100 (volume ratio)).

Methods of the "crystallization from a vapor" include, for example, a gasification method (sealed tube method, gas stream method), a gas phase reaction method, a chemical transportation method, and so forth.

Methods of the "crystallization from a molten form" include, for example, a normal freezing method (pulling-up method, temperature gradient method, Bridgman method), a zone melting method (zone leveling method, float zone method), a special growth method (VLS method, liquid phase epitaxis method), and so forth.

Incidentally, the crystallization of the salt of (R)-lansoprazole is usually carried out through the use of (1) crystallization due to cooling a solvent solution (organic solvent solution such as an alcohol, an ether and a hydrocarbon) heated to about 50 to 120° C. (preferably about 70 to 100° C.) in which (R)-lansoprazole is dissolved, or (2) crystallization due to addition of a poor solvent into the solvent solution (in particular, concentrated liquid). According to such a crystallization method, a solvated crystal can be also obtained, and an absolute crystal can be also obtained by heat-treating a mixture solution containing (R)-lansoprazole and a solvent to a high temperature (e.g., a reflux temperature of the solvent) and cooling.

For analyzing the resultant crystal, X-ray diffraction crystallographic analysis is commonly used. In addition, crystal orientation can also be determined by a mechanical method, an optical method, etc.

The salt of the present invention is useful as a pharmaceutical because of excellent antiulcer action of the salt, gastric acid secretion-inhibiting action, mucosa-protecting action, anti-*Helicobacter pylori* action, etc., and low toxicity of the salt. Furthermore, the salt has a high purity and an excellent stability, and can be stored at a room temperature for a long period of time, in addition ensures simple handling thereof, as a result, a solid pharmaceutical composition can be produced from the salt with advantageous reproducibility. In addition, when orally administered, the salt of the present invention is excellent in solubility and absorbability and more rapidly expresses an action or effect thereof. Moreover, when the salt of the present invention is administered, a Cmax (maximum blood concentration) and an AUC (area under the concentration-time curve) are increased, and the salt tends to be metabolized with difficulty because of an increased protein-binding rate, prolonging a duration of action or effectiveness. The salt of the present invention is therefore useful as a pharmaceutical of low doses and low prevalence of adverse reactions. In particular, the crystal of the salt of the present invention is highly pure and has an improved stability (see Experimental Example 1). Further, the crystal of the salt of the present invention ensures an increased protein-binding rate and a prolonged length of effectiveness, in addition, is advantageous to handling and operatability in a preparation of a pharmaceutical.

Incidentally, with respect to the crystal, not all compounds and salts inclusive of the salt of the present invention can be crystallized, but the salt of the present invention has been obtained in the form of a crystal for the first time, and the inventors of the present invention found that the salt and the crystal thereof have excellent properties as a pharmaceutical, as described above.

The salt of the present invention is also useful in mammals (e.g., human beings, nonhumans such as monkeys, sheep, bovines, horses, dogs, cats, rabbits, rats, mice, etc.) for the treatment and prophylaxis (or prevention) of digestive ulcer (peptic ulcer) (e.g., gastric ulcer, duodenal ulcer, stomal ulcer, Zollinger-Ellison syndrome, etc.), gastritis, reflux esophagitis, NUD (Non-Ulcer Dyspepsia), gastric cancer (inclusive of gastric ulcer accompanied with an enhanced production of interleukin-1β due to genetic polymorphism of interleukin-1), gastric MALT lymphoma; disease due to *Helicobacter pylori;* upper gastrointestinal hemorrhage due to digestive ulcer, acute stress ulcer and hemorrhagic gastritis; upper gastrointestinal hemorrhage due to invasive stress (stress from major surgery necessitating intensive management after surgery, and from cerebral vascular disorder, head trauma, multiple organ failure and extensive burn necessitating intensive treatment); and ulcer caused by a nonsteroidal anti-inflammatory agent. Further, the salt of the present invention is also useful for *Helicobacter pylori* eradication; suppression of the above upper gastrointestinal hemorrhage; treatment and prophylaxis of hyperacidity and ulcer due to postoperative stress; pre-anesthetic administration etc.

The salt of the present invention is of low toxicity and can be safely administered orally or non-orally (e.g., topical, rectal and intravenous administration, etc.), as such or in the form of pharmaceutical compositions formulated with a pharmacologically acceptable carrier, e.g., solids (tablets (including sugar-coated tablets and film-coated tablets), powders, granules, capsules (including soft capsules), orally disintegrating tablets, suppositories), liquids (including injectable preparations), ointments, cataplasms or the like in accordance with a commonly known method. The pharmaceutical composition can be also administrated as sustained-release preparations or targets (target agents) by utilizing a drug delivery system. That is, the salt of the present invention is advantageously used for producing a pharmaceutical composition for prophylaxis and treatment of the above disease, *Helicobacter pylori* eradication, suppression of the above upper gastrointestinal hemorrhage, pre-anesthetic administration etc.

The content of the salt of the present invention in the pharmaceutical composition of the present invention is about 0.01 to 100% by weight relative to the entire or whole composition. Varying depending on a subject of administration, a route of administration, a target disease etc., the dose of the salt as an active ingredient is about 0.5 to 1,500 mg/day, and preferably about 5 to 150 mg/day, for example, when the salt is orally administered as an antiulcer agent to an adult human (60 kg). The salt of the present invention may be administered once daily or in 2 to 3 divided doses per day.

Pharmacologically acceptable carriers that may be used for producing the pharmaceutical composition of the present invention include various organic or inorganic carrier substances in common use as pharmaceutical materials, including excipients, lubricants, binders, disintegrants, water-soluble polymers and basic inorganic salts for solid preparations; and solvents, dissolution aids, suspending agents, isotonizing agents, buffers and soothing agents or pain-relieving agents for liquid preparations. Other ordinary pharmaceutical additives such as preservatives, antioxidants, coloring agents, sweetening agents, souring agents, bubbling agents and flavorings may also be used if necessary.

The "excipients" include, for example, lactose, sucrose, D-mannitol, a starch, a cornstarch, a crystalline cellulose, a light silicic anhydride and titanium oxide.

The "lubricants" include, for example, magnesium stearate, a sucrose fatty acid ester, a polyethylene glycol, talc and stearic acid.

The "binders" include, for example, cellulose derivatives (a hydroxyethyl cellulose, a hydroxypropyl cellulose, a hydroxypropylmethyl cellulose, a low-substituted hydroxypropyl cellulose, an ethyl cellulose, a carboxymethyl cellulose sodium, a-crystalline cellulose etc.), a starch, a polyvinylpyrrolidone, a polyvinylalcohol, a gum arabic powder, a gelatin, a pullulan and the like.

The "disintegrants" include (1) a crosslinked povidone, (2) what is called super-disintegrants such as crosslinked carmellose sodium (FMC-Asahi Chemical) and carmellose calcium (Gotoku Chemical Company Ltd.), (3) a carboxymethyl starch sodium (e.g., product of Matsutani Chemical Industry Co., Ltd.), (4) a low-substituted hydroxypropyl cellulose (e.g., product of Shin-Etsu Chemical Co., Ltd.), (5) a cornstarch, and so forth. The "crosslinked povidone" may be any crosslinked polymer having the chemical name 1-ethenyl-2-pyrrolidinone homopolymer, including a polyvinylpyrrolidone (PVPP) and a 1-vinyl-2-pyrrolidinone homopolymer, and is exemplified by Colidon CL (produced by BASF), Polyplasdon XL (produced by ISP), Polyplasdon XL-10 (produced by ISP) and Polyplasdon INF-10 (produced by ISP).

The "water-soluble polymers" include, for example, ethanol-soluble and water-soluble polymers [e.g., cellulose derivatives such as a hydroxypropyl cellulose (hereinafter also referred to as HPC), a polyvinylpyrrolidone] and ethanol-insoluble and water-soluble polymers [e.g., cellulose derivatives such as a hydroxypropylmethyl cellulose (hereinafter also referred to as HPMC), a methyl cellulose and a carboxymethyl cellulose sodium, a sodium polyacrylate, a polyvinyl alcohol, a sodium alginate, a guar gum].

The "basic inorganic salts" include, for example, basic inorganic salts of sodium, potassium, magnesium and/or calcium. Preferred are basic inorganic salts of magnesium and/or calcium. More preferred are basic inorganic salts of magnesium. The basic inorganic salts of sodium include, for example, sodium carbonate, sodium hydrogencarbonate, disodium hydrogenphosphate, etc. The basic inorganic salts of potassium include, for example, potassium carbonate, potassium hydrogencarbonate, etc. The basic inorganic salts of magnesium include, for example, heavy magnesium carbonate, magnesium carbonate, magnesium oxide, magnesium hydroxide, magnesium metasilicate aluminate, magnesium silicate, magnesium aluminate, synthesized hydrotalcite [$Mg_6Al_2(OH)_{16}.CO_3.4H_2O$], alumina hydroxide magnesium, and so forth. Among others, preferred is heavy magnesium carbonate, magnesium carbonate, magnesium oxide, magnesium hydroxide, etc. The basic inorganic salts of calcium include, for example, precipitated calcium carbonate, calcium hydroxide, etc.

The "solvents" include, for example, water for injection, alcohols (e.g., ethanol), ethylene glycol, propylene glycol, macrogol, fats and oils (e.g., a sesame oil, a corn oil and an olive oil).

The "dissolution aids" include, for example, a polyethylene glycol, propylene glycol, D-mannitol, benzyl benzoate, ethanol, trisaminomethane, cholesterol, triethanolamine, sodium carbonate and sodium citrate.

The "suspending agents" include, for example, surfactants (anionic, cationic, nonionic, or amphoteric surfactants) such as stearyltriethanolamine, sodium laurylsulfate, laurylaminopropionic acid, lecithin, benzalkonium chloride, benzethonium chloride and monostearic glycerol, a polyoxyethylene glycerin fatty acid ester, a sorbitane fatty acid ester, a polyoxyethylenesorbitane fatty acid ester, a polyoxyethylene-polyoxypropylene block copolymer; and hydrophilic polymers such as a polyvinyl alcohol, a polyvinylpyrrolidone, a carboxymethyl cellulose sodium, a methyl cellulose, a hydroxymethyl cellulose, a hydroxyethyl cellulose and a hydroxypropyl cellulose.

The "isotonizing agents" include, for example, glucose, D-sorbitol, D-mannitol, sodium chloride, glycerol and the like.

The "buffers" include, for example, buffer solutions of phosphates, acetates, carbonates, citrates, borates or the like.

The "soothing agents" include, for example, benzyl alcohol and the like.

The "preservatives" include, for example, p-oxybenzoic acid esters, chlorobutanol, benzyl alcohol, phenethyl alcohol, dehydroacetic acid and sorbic acid or salts thereof.

The "antioxidants" include, for example, sulfites, ascorbic acid and α-tocopherol.

The "coloring agents" include, for example, food colors such as Food Color Yellow No. 5, Food Color Red No. 2 and Food Color Blue No. 2; and food lake colors, colcothar and the like.

The "sweetening agents" include, for example, sugars, saccharin sodium, dipotassium glycyrrhizinate, aspartame, stevia, thaumatin and the like.

The "souring agents" include, for example, citric acid (citric anhydride), tartaric acid and malic acid.

The "bubbling agents" include, for example, sodium bicarbonate.

The "flavorings" may be synthetic substances or naturally occurring substances, and include, for example, lemon, lime, orange, menthol and strawberry.

The salt of the present invention may be prepared as a preparation for an oral administration in accordance with per se known methods, for example, by compression-shaping or molding a mixture containing the salt, an excipient, a disintegrant, a binder, a lubricant, or the like, and subsequently coating the resultant product if necessary by per se known methods for the purpose of taste masking, enteric dissolution or sustained release. For an enteric preparation, an intermediate layer may be provided by a commonly known method between the enteric layer and the drug-containing layer for the purpose of separation of the two layers.

For preparing the salt of the present invention as an orally disintegrating tablet, for example, the following method is available, wherein;

a core containing a crystalline cellulose and lactose is coated with the salt of the present invention and, if necessary, a basic inorganic salt, and is further coated with a coating layer containing a water-soluble polymer to form a composition, the composition is coated with an enteric coating layer containing a polyethylene glycol, further coated with an enteric coating layer containing triethyl citrate, still further coated with an enteric coating layer containing a polyethylene glycol, and still yet further coated with mannitol to form fine granules, and the fine granules are mixed with additives to be shaped or molded. The above-mentioned "enteric coating layer" includes, for example, aqueous enteric polymer substrates such as a cellulose acetate phthalate (CAP), a hydroxypropylmethyl cellulose phthalate, a hydroxymethyl cellulose acetate succinate, (meth)acrylic acid copolymers [e.g., Eudragit L30D-55 (trade name; produced by Rohm), Colicoat MAE30DP (trade name; produced by BASF), Polykid PA30 (trade name; produced by San-yo Chemical)], a carboxymethylethyl cellulose and a shellac; sustained-release substrates such as (meth)acrylic acid copolymers [e.g., Eudragit NE30D (trade name), Eudragit RL30D (trade name). Eudragit RS30D (trade name), etc.]; water-soluble polymers; plasticizers such as triethyl citrate, a polyethylene glycol, an acetylated monoglyceride, a triacetine and a castor oil; and mixtures thereof. The above-mentioned "additive" includes, for example, water-soluble sugar alcohols (e.g., sorbitol, mannitol, multitol, reduced starch saccharides, xylitol, reduced paratinose, erythritol, etc.), crystalline celluloses [e.g., Ceolas KG 801, Avicel PH 101, Avicel PH 102, Avicel PH 301, Avicel PH 302, Avicel RC-591 (a crystalline cellulose carmellose sodium)], and low-substituted hydroxypropyl celluloses [e.g., LH-22, LH-32, LH-23, LH-33 (Shin-Etsu Chemical Co., Ltd.) and mixtures thereof]; and binders, souring agents, bubbling agents, sweetening agents, flavorings, lubricants, coloring agents, stabilizers, excipients, disintegrants etc. are also used.

The salt of the present invention may be used in combination with other ingredients (e.g., 1 to 3 other active ingredients).

The "other active ingredients" include, for example, substances having an anti-*Helicobacter pylori* action, imidazole-series compounds, bismuth salts, quinolone-series compounds, and so forth. Of these substances, preferred are substances having an anti-*Helicobacter pylori* action, imidazole-series compounds etc. The "substances having an anti-*Helicobacter pylori* action" include, for example, antibiotic penicillins (e.g., amoxicillin, benzylpenicillin, piperacillin, mecillinam, etc.), antibiotic cefems (e.g., cefixime, cefaclor, etc.), antibiotic macrolides (e.g., antibiotic erythromycins such as erythromycin, clarithromycin etc.), antibiotic tetracyclines (e.g., tetracycline, minocycline, streptomycin, etc.), antibiotic aminoglycosides (e.g., gentamicin, amikacin, etc.), imipenem, and so forth. Of these substances, preferred are antibiotic penicillins, antibiotic macrolides etc. The "imidazole-series compounds" include, for example, metronidazole, miconazole, etc. The "bismuth salts" include, for example, bismuth acetate, bismuth citrate, etc. The "quinolone-series compounds" include, for example, ofloxacin, ciploxacin, etc. In particular, it is preferred for *Helicobacter pylori* eradication that the salt of the present invention is used in combination with antibiotic penicillins (e.g., amoxicillin) and/or antibiotic erythromycins (e.g., clarithromycin).

The "other active ingredients" and the salt of the present invention may also be used in combination as a mixture prepared as a single pharmaceutical composition [e.g., tablets, powders, granules, capsules (including soft capsules), liquids, injectable preparations, suppositories, sustained-release preparations, etc.], in accordance with per se known methods, and may also be prepared as separate preparations and administered to the same subject simultaneously or at a time interval.

INDUSTRIAL APPLICABILITY

The salt of the present invention is useful as a pharmaceutical because the salt is excellent in an antiulcer action, a gastric acid secretion-inhibiting action, a mucosa-protecting action, an anti-*Helicobacter pylori* action etc., and because the salt is of low toxicity. Furthermore, the salt has a high purity and an excellent stability, and ensures a storage thereof at a room temperature for a long period of time, in addition simplifies a handling thereof, as a result, the salt ensures a production of a solid pharmaceutical composition with advantageous reproducibility. In addition, when orally administered, the salt of the present invention is excellent in solubility and absorbability, and an action or effect thereof is rapidly expressed. Moreover, when the salt of the present invention is administered, a Cmax (maximum blood concentration) and an AUC (area under the concentration-time curve) are increased, and the salt tends to be metabolized with difficulty because of an increased protein-binding rate, prolonging a duration of action or effectiveness. The salt of the present invention is therefore useful as a pharmaceutical of low doses and low prevalence of adverse reactions. In particular, the crystal of the salt of the present invention ensures a high purity, an improved stability, and an increased protein-binding rate and a prolonged length of effectiveness, in addition, is advantageous to handling and operatability in a preparation of a pharmaceutical.

EXAMPLES

The following reference example and examples are intended to describe this invention in further detail and should by no means be interpreted as defining the scope of the invention.

In the following reference example and examples, the term "a room temperature" indicates about 15 to 30° C.

$^1$H-NMR spectra were determined with CDCl$_3$ or DMSO-d$_6$ as the solvent using a Varian Gemini-200; data are shown in chemical shift δ (ppm) from the internal standard tetramethylsilane.

IR was determined using a SHIMADZU FTIR-8200.

Optical rotation [α]$_D$ was determined at 20° C. using a DIP-370 Digital polarimeter (produced by JASCO).

X-ray powder diffraction was determined using a X-ray Powder Diffraction meter Rigaku RINT2500 (ultraX18) No. PX-3.

Optical purity (%ee) was determined by high performance liquid chromatography with use of a chiral column in accordance with the following conditions.

Conditions of high performance liquid chromatography;
 column: CHIRALCEL OD (manufactured by Daicel Chemical Industries, Ltd.)
 mobile phase: hexane/ethanol=90/10
 flow rate: 1.0 ml/min
 detection wavelength: UV 285 nm
 The other symbols used herein have the following definitions:
s: singlet
d: doublet
t: triplet
q: quartet
m: multiplet
bs: broad singlet
J: a coupling constant Reference Example 1

(R)-2-[[[3-methyl-4-(2,2,2-trifluoroethoxy)-2-pyridyl]methyl]sulfinyl]benzimidazole In a stream of nitrogen, 2-[[[3-methyl-4-(2,2,2-trifluoroethoxy)-2-pyridyl]methyl]thio]benzimidazole (4.5 kg, 12.7 mol, water content of 1.89 g), toluene (22 L), water (25 g, 1.39 mol, total water content of 1.49 mol) and (+)-diethyl tartrate (0.958 L, 5.60 mol) were mixed. In a stream of nitrogen, to the mixture was added titanium(IV) isopropoxide (0.747 L, 2.53 mol) at 50 to 60° C., and stirred for 30 minutes at the same temperature. In a stream of nitrogen, to the resulting mixture liquid was added diisopropylethylamine (0.733 L, 4.44 mol) at a room temperature, further added cumenehydroperoxide (6.88 L, content of 82%, 37.5 mol) at −5 to 5° C., and stirred at −5 to 5° C. for 1.5 hours to obtain a liquid reaction mixture. In a stream of nitrogen, to the reaction liquid was added 30% sodium thiosulfate aqueous solution (17 L) to decompose residual cumenehydroperoxide. The reaction liquid was phase-separated, and water (4.5 L), heptane (13.5 L), t-butyl methyl ether (18 L) and heptane (27 L) were successively added to the resulting organic phase, and the mixture was subjected to crystallization under stirring. The resulting crystal was separated and washed with t-butyl methyl ether-toluene (t-butyl methyl ether:toluene=4:1) (4 L). Under stirring, an acetone (20 L) suspension of the wet crystal was added dropwise to a liquid mixture of acetone (7 L) and water (34 L), and then added water (47 L) thereto. The precipitated crystal was separated and washed with acetone-water (acetone:water=1:3) (4 L) and with water (12 L). The wet crystal was dissolved in ethyl acetate (45 L) and water (3 L) to be phase-separated. A slight amount of insoluble matter (undissolved material) in an organic phase was filtrated off, and then triethylamine (0.2 L) was added to the organic phase and concentrated under a reduced pressure until the liquid volume of the organic phase was to about 7 L. To the resultant condensate were added methanol (2.3 L), about 12.5% aqueous ammonia (23 L) at about 50° C. and t-butyl methyl ether (22 L) at about 50° C. to be phase-separated. To the resultant organic phase was added about 12.5% aqueous ammonia (11 L) to be phase-separated (the operation was repeated once). The aqueous phases were combined with each other, ethyl acetate (22 L) was added thereto, and under cooling, acetic acid was added dropwise thereto for adjusting pH to about 8. The resulting liquid was phase-separated and the resultant aqueous phase was extracted with ethyl acetate (11 L). The organic phases were combined with each other, and washed with about 20% brine (11 L). After adding triethylamine (0.2 L), the organic phase was concentrated under a reduced pressure. To the concentrate was added acetone (5 L) and concentrated under a reduced pressure. The resulting concentrate was dissolved in acetone (9 L), the resulting mixture was added dropwise to a mixture liquid of acetone (4.5 L) and water (22.5 L), and then water (18 L) was added dropwise thereto. The precipitated crystal was separated, and was washed with cold acetone-water (acetone:water=1:3) (3 L) and water (12 L), successively. The wet crystal was dissolved in ethyl acetate (32 L). The separated aqueous phase was separated by separation operation, and the resulting organic phase was concentrated under a reduced pressure until the liquid volume became to be about 14 L. To the residue were added ethyl acetate (36 L) and active carbon (270 g), and after stirring, active carbon was filtered off. The resultant filtrate was concentrated under a reduced pressure until the liquid volume was to about 14 L. To the concetrate was added dropwise heptane (90 L) at about 40° C. After stirring at the same temperature for about 30 minutes, the resultant crystal was separated, and washed with ethyl acetate-heptane (ethyl acetate:heptane=1:8, 6L) at about 40° C. After drying, the title compound (3.4 kg) was obtained. The enantiomer excess rate of the compound was 100%ee.

Example 1

The Crystal of Sodium Salt of (R)-2-[[[3-methyl-4-(2,2,2-trifluoroethoxy)-2-pyridinyl]methyl]sulfinyl]-1H-benzimidazole To ethanol solution (50 mL) of (R)-2-[[[3-methyl-4-(2,2,2-trifluoroethoxy)-2-pyridinyl]methyl]sulfinyl]-1H-benzimidazole (5.00 g) was added 1N sodium hydroxide aqueous solution (13.5 mL) under cooling with an ice. After filtration, the filtrate was concentrated under a reduced pressure. The residue was dissolved by adding ethanol (50 mL), and the resultant solution was concentrated under a reduced pressure. The residue was repeatedly dissolved by adding ethanol (50 mL) and the resultant solution was concentrated under a reduced pressure. To the resulting foamy material was added diethyl ether (50 mL), and then the resultant mixture was subjected to an ultrasonic treatment, and was heated with refluxing for 30 minutes. After cooling the mixture to a room temperature, the precipitated solid was filtrated off and the resultant solid was washed with diethyl ether (10 mL). The solid was suspended in diethyl ether (50 mL), and the suspension was heated with refluxing for 30 minutes. After cooling the suspension to a room temperature, the precipitated solid was filtrated, and washed with diethyl ether (10 mL). The solid was suspended in diethyl ether (50 mL) again and the suspension was heated with refluxing for 1 hour. After cooling the resulting suspension to a room temperature, the precipitated solid was filtered, washed with diethyl ether (10 mL) and dried under a reduced pressure at 60° C. to obtain 3.70 g of white powder.

The resulting white powder (0.50 g) was suspended in a mixture solution of ethanol (0.5 mL) and toluene (50 mL), and was the suspension heated with refluxing for 16 hours with use of a reactor equipped with a tube for dehydration charged with molecular sieve. After cooling the resulting mixture to a room temperature, the precipitated solid was filtrated and washed twice with toluene (5 mL). After drying at 60° C. under a reduced pressure, the title compound (0.48 g) was obtained. The data of X-ray powder diffraction is shown in Table 1, and the chart of X-ray powder diffraction is shown in FIG. 1.

Elemental Analysis

Calculated (as $C_{16}H_{13}N_3O_2SF_3Na$): C, 49.11; H, 3.35; N, 10.74; S, 8.19; F, 14.56. Found: C, 48.80; H, 3.51; N, 10.62; S, 8.34; F, 14.29.

Na content by atomic absorption spectrometry: 6.0% (Calculated: 5.87%)

$^1$H-NMR (DMSO-$d_6$): 2.21 (3H, s), 4.46 (1H, d, J=13.0 Hz), 4.78 (1H, d, J=13.0 Hz), 4.90 (2H, q, J=8.8 Hz), 6.89–6.94 (2H, m), 7.08 (1H, d, J=5.8 Hz), 7.45–7.51 (2H, m), 8.36 (1H, d, J=5.8 Hz)

IR (vcm$^{-1}$): 3400, 1584, 1474, 1454, 1377, 1312, 1265, 1167, 1113

$[\alpha]_D$=+107.9° (c=0.999%, MeOH)

TABLE 1

| 2θ (°) | half-value width | d-value [Å] | relative intensity [%] |
|---|---|---|---|
| 5.880 | 0.118 | 15.0181 | 100 |
| 11.740 | 0.165 | 7.5317 | 30 |
| 12.540 | 0.165 | 7.0530 | 19 |
| 16.000 | 0.141 | 5.5347 | 10 |
| 21.280 | 0.141 | 4.1719 | 11 |
| 22.440 | 0.188 | 3.9588 | 14 |
| 26.020 | 0.188 | 3.4216 | 11 |
| 26.760 | 0.165 | 3.3287 | 10 |

Example 2

Figure 2:
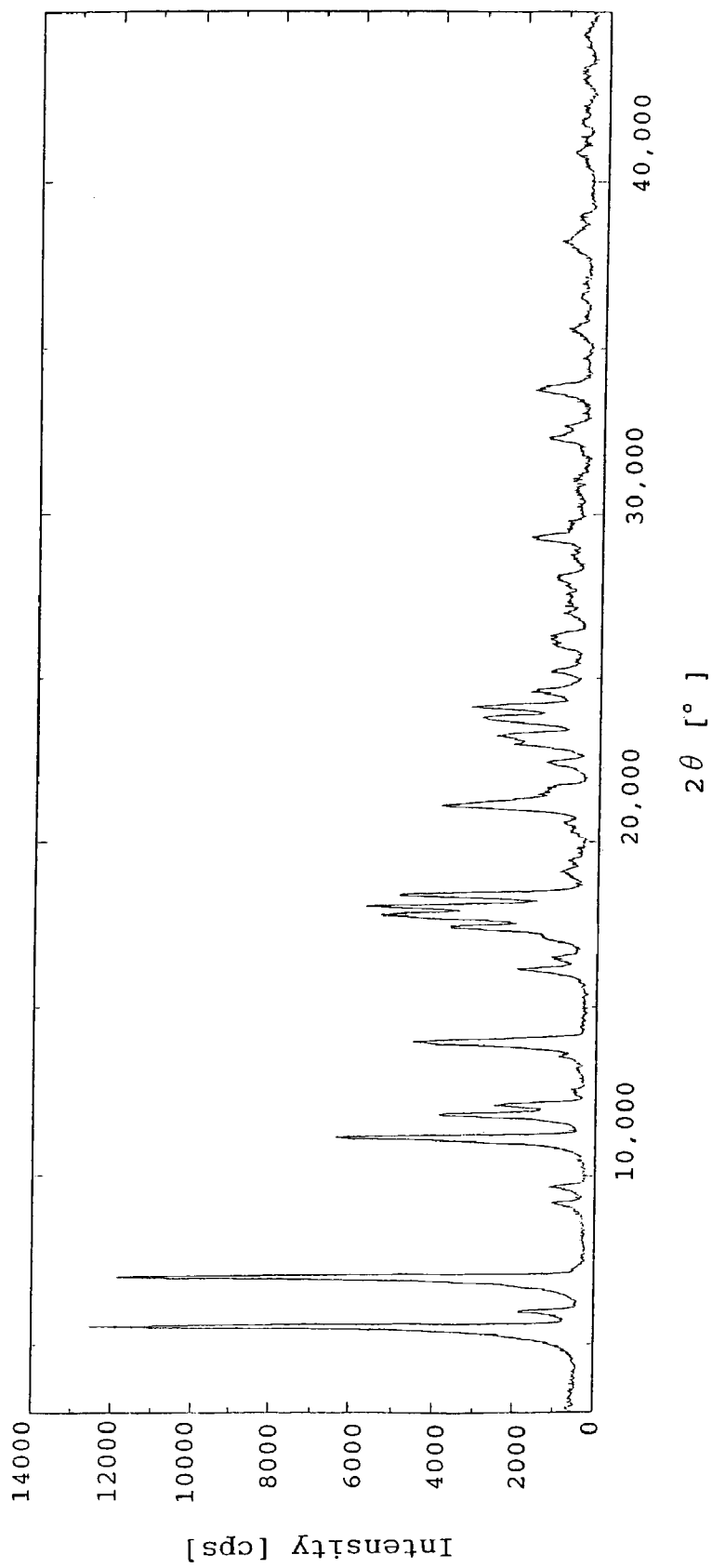
FIG. 2 is the X-ray powder diffraction analysis chart of the crystal of Example 2.

The crystal solvated with isopropyl alcohol of sodium salt of (R)-2-[[[3-methyl-4-(2,2,2-trifluoro-ethoxy)-2-pyridyl]methyl]sulfinyl]benzimidazole To (R)-2-[[[3-methyl-4-(2,2,2-trifluoroethoxy)-2-pyridyl]methyl]sulfinyl]benzimidazole (150.0 g, 0.41 mol) was added methanol (225 mL) to dissolve, and 20% sodium hydroxide aqueous solution (81 g, 0.41 mol) was added thereto. The mixture was concentrated under a reduced pressure. To the residue was added isopropyl alcohol (1,500 mL) to dissolve, and the resultant mixture was stirred at a room temperature for about 24 hours. The precipitated crystal was separated and washed with isopropyl alcohol (300 mL). After drying at 40° C. under a reduced pressure, the title crystal (142.0 g) was obtained. The data of X-ray powder diffraction is shown in Table 2, and the chart of X-ray powder diffraction is shown in FIG. 2.

Elemental Analysis

Calculated (as $C_{16}H_{13}N_3O_2SF_3Na \cdot C_3H_8O \cdot 1.5H_2O$): C, 47.70; H, 5.06; N, 8.78; S, 6.70; F, 11.91. Found: C, 47.68; H, 5.02; N, 8.70; S, 7.00; F, 11.84.

Na content by atomic absorption spectrometry: 4.8% (Calculated: 4.80%)

TABLE 2

| 2θ (°) | half-value width | d-value [Å] | relative intensity [%] |
|---|---|---|---|
| 5.520 | 0.141 | 15.9967 | 98 |
| 6.980 | 0.165 | 12.6536 | 100 |
| 11.080 | 0.165 | 7.9788 | 54 |
| 11.780 | 0.165 | 7.5062 | 32 |
| 13.940 | 0.235 | 6.3476 | 36 |
| 17.400 | 0.188 | 5.0924 | 29 |
| 17.760 | 0.235 | 4.9900 | 43 |
| 18.020 | 0.141 | 4.9186 | 48 |
| 18.380 | 0.188 | 4.8230 | 42 |
| 21.100 | 0.212 | 4.2070 | 30 |

Example 3

Figure 3:
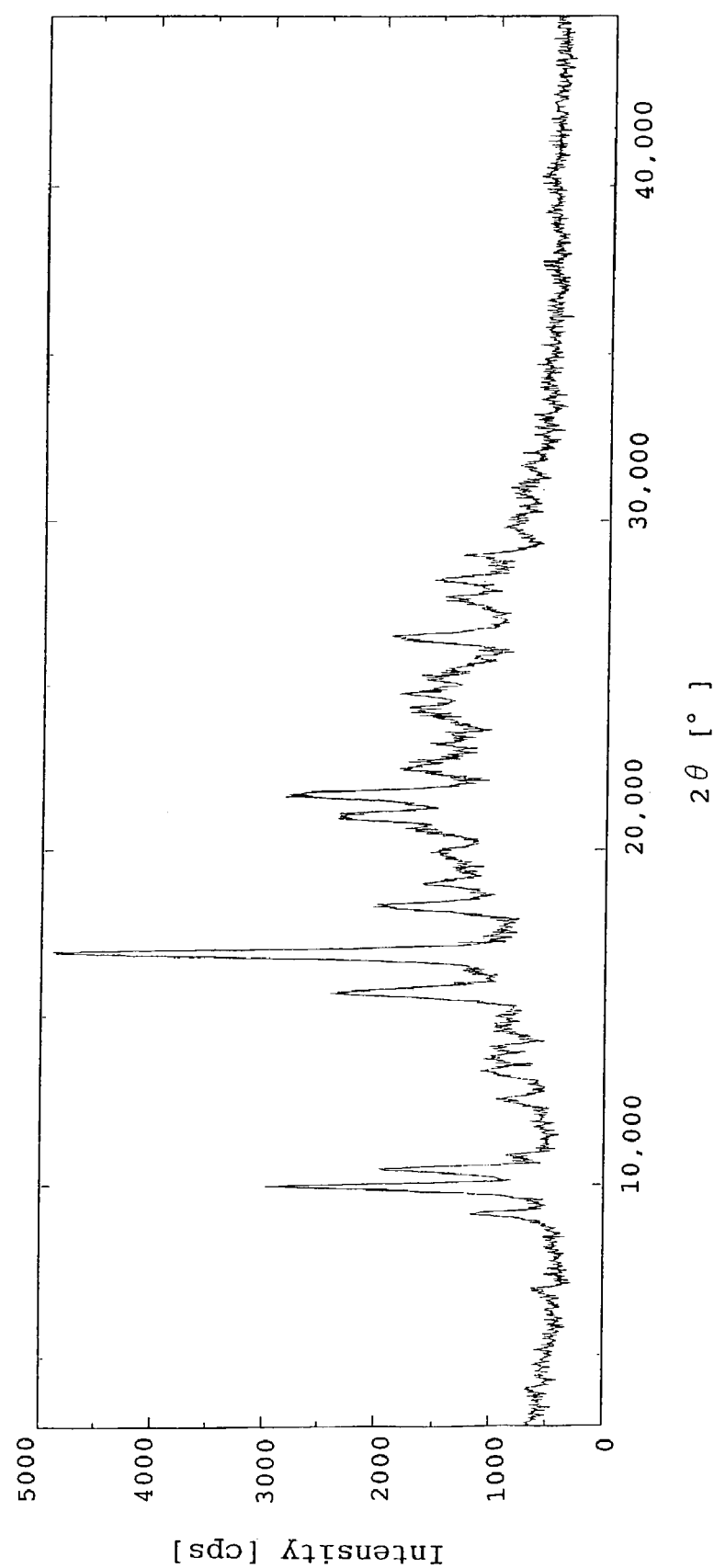
FIG. 3 is the X-ray powder diffraction analysis chart of the crystal of Example 3.

The crystal of sodium salt of (R)-2-[[[3-methyl-4-(2,2,2-trifluoroethoxy)-2-pyridyl]methyl]sulfinyl]benzimidazole Monohydrate To (R)-2-[[[3-methyl-4-(2,2,2-trifluoroethoxy)-2-pyridyl]methyl]sulfinyl]benzimidazole (50.0 g, 0.14 mol) was added sodium hydroxide (5.4 g, 0.14 mol), water (100 mL) and methanol (120 mL) to dissolve, and the mixture was concentrated under a reduced pressure. To the residue was added water (20 mL) to crystallize, and the resultant was stirred for about 1 hour under cooling with an ice. The precipitated crystal was separated and washed with water (100 mL). The crystal was dried at 40° C. under a reduced pressure. To the dried crystal were added isopropyl alcohol (158.3 mL) and water (31.7 mL), the mixture was stirred and concentrated until the liquid volume was reduced to about 100 mL. Isopropyl alcohol (100 mL) was added thereto to crystallize, and the resultant was stirred at a room temperature for about 1 hour. The precipitated crystal was separated and washed with isopropyl alcohol (100 mL). The crystal was dried at 40° C. under a reduced pressure. To the dried crystal was added water (340 mL) and the mixture was stirred at a room temperature for about 3 hours. The precipitated crystal was separated and washed with water (100 mL). After drying at 40° C. under a reduced pressure, the title crystal (20.0 g) was obtained. The data of X-ray powder diffraction is shown in Table 3, and the chart of X-ray powder diffraction is shown in FIG. 3.

Elemental Analysis

Calculated (as $C_{16}H_{13}N_3O_2SF_3Na \cdot H_2O$): C, 46.94; H, 3.69; N, 10.26; S, 7.83; F, 13.92. Found: C, 47.04; H, 3.67; N, 10.27; S, 7.75; F, 13.93.

Na content by atomic absorption spectrometry: 5.6% (Calculated: 5.62%)

TABLE 3

| 2θ (°) | half-value width | d-value [Å] | relative intensity [%] |
|---|---|---|---|
| 9.940 | 0.188 | 8.8912 | 57 |
| 10.440 | 0.212 | 8.4665 | 35 |

TABLE 3-continued

| 2θ (°) | half-value width | d-value [Å] | relative intensity [%] |
|---|---|---|---|
| 15.700 | 0.306 | 5.6398 | 40 |
| 16.900 | 0.259 | 5.2419 | 100 |
| 18.300 | 0.259 | 4.8439 | 30 |
| 20.960 | 0.141 | 4.2348 | 37 |
| 21.120 | 0.141 | 4.2031 | 35 |
| 21.720 | 0.282 | 4.0883 | 45 |
| 24.740 | 0.141 | 3.5957 | 25 |
| 26.480 | 0.306 | 3.3632 | 27 |

Example 4

The magnesium salt of (R)-2-[[[3-methyl-4-(2,2,2-trifluoroethoxy)-2-pyridinyl]methyl]sulfinyl]-1H-benzimidazole (R)-2-[[[3-methyl-4-(2,2,2-trifluoroethoxy)-2-pyridinyl]methyl]sulfinyl]-1H-benzimidazole (1.11 g, 3.0 mmol) was dissolved in methanol (10 mL), and 25% aqueous ammonia (0.34 mL, 4.5 mmol) and then magnesium sulfate heptahydrate (555 mg, 2.25 mmol) were added thereto. After stirring at a room temperature overnight, an insoluble matter was filtrated off, and the filtrate was concentrated under a reduced pressure. The residue was dissolved in methanol (10 mL) again, and water (10 mL) was slowly added dropwise thereto with stirring. After stirring for about 4 hours, the precipitated solid was filtrated, washed with water-methanol (4:1) and dried under a reduced pressure to obtain crude magnesium salt in the form of a colorless amorphous (747 mg). To the crude magnesium salt (720 mg) was added ethanol-ether (ethanol:ether=5:95, 20 mL). After ultrasonic treating the mixture and successively heating the mixture to about 35° C., the salt was filtrated and washed with ether. The same operation was repeated. The resulting powder solid was dissolved in ethanol (2 mL), and ether (40 mL) was gradually added dropwise thereto with stirring. After stirring overnight, the precipitated solid was filtrated and washed with ether. After drying the solid at 60° C. under a reduced pressure, the title compound (430 mg) was obtained as an amorphous.

Elemental Analysis
Calculated (as $C_{32}H_{26}N_6O_4S_2F_6Mg.4.5H_2O$): C, 45.64; H, 4.19; N, 9.98. Found: C, 45.67; H, 4.19; N, 9.80.

Mg content by atomic absorption spectrometry: 2.9% (Calculated: 2.89%)

Water content result evaluated: 8.7%

Example 5

The magnesium salt of (R)-2-[[[3-methyl-4-(2,2,2-trifluoroethoxy)-2-pyridinyl]methyl]sulfinyl]-1H-benzimidazole To (R)-2-[[[3-methyl-4-(2,2,2-trifluoroethoxy)-2-pyridinyl]methyl]sulfinyl]-1H-benzimidazole (5.0 g, 0.014 mol) were added 8% magnesium ethoxide (6.5 g, 0.006 mol) and methanol (5 mL) to dissolve. The mixture was concentrated under a reduced pressure, and to the residue was added tert-butyl methyl ether (100 mL) to crystallize. The precipitated solid was separated and washed with tert-butyl methyl ether (10 mL). After drying at 40° C. under a reduced pressure, the title compound (4.4 g) was obtained as an amorphous.

Elemental Analysis
Calculated (as $C_{32}H_{26}N_6O_4S_2F_6Mg.1.5CH_3OH.2.5H_2O$): C, 47.11; H, 4.37; N, 9.84; S, 7.51; F, 13.35. Found: C, 47.21; H, 4.40; N, 9.79; S, 7.58; F, 13.21.

Mg content by atomic absorption spectrometry: 2.8% (Calculated: 2.85%)

Example 6

The crystal of potassium salt of (R)-2-[[[3-methyl-4-(2,2,2-trifluoroethoxy)-2-pyridinyl]methyl]sulfinyl]-1H-benzimidazole To an ethanol solution (10 mL) of (R)-2-[[[3-methyl-4-(2,2,2-trifluoroethoxy)-2-pyridinyl]methyl]sulfinyl]-1H-benzimidazole (1.00 g) was added 10% potassium hydroxide aqueous solution (1.53 mL) under cooling with an ice. After concentrating the mixture under a reduced pressure, the residue was dissolved by adding ethanol (10 mL), and concentrated under a reduced pressure. The residue was repeatedly dissolved by adding ethanol (10 mL) and the resultant mixture was concentrated under a reduced pressure. To the resulting foamy material was added diethyl ether (10 mL), and after ultrasonic treatment, the mixture was allowed to stand and supernatant was removed off. Another diethyl ether (10 mL) was added to the resultant precipitated resudue, and after ultrasonic treatment, the resultant mixture was allowed to stand and supernatant was removed off. Diethyl ether (10 mL) was added to the residue, and the resultant mixture was stirred for 20 minutes. Then, the precipitated solid was filtrated and washed with diethyl ether (10 mL). The resultant solid was dried at 60° C. under a reduced pressure to give 0.951 g of white powder.

Figure 4:
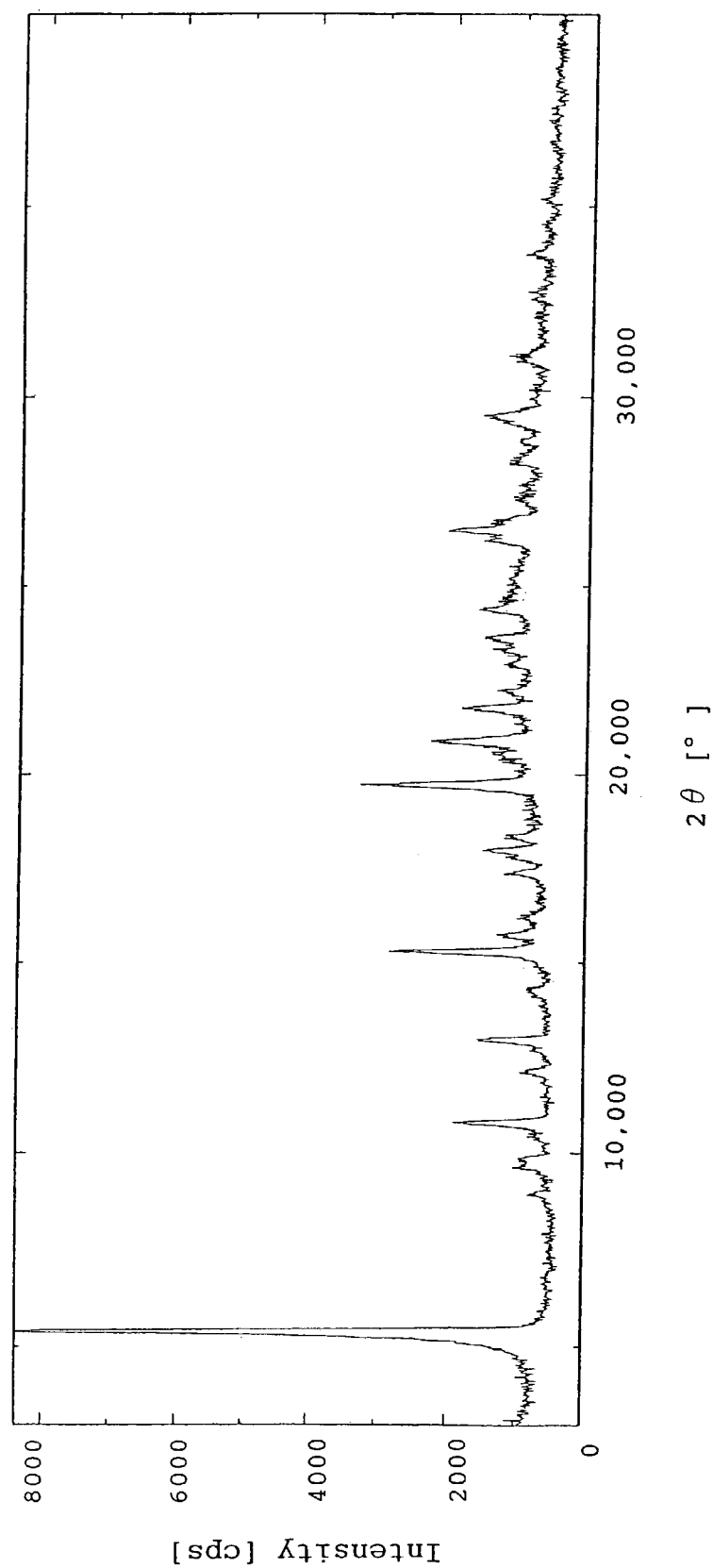
FIG. 4 is the X-ray powder diffraction analysis chart of the crystal of Example 6.

The resulting white powder (0.43 g) was suspended in diethyl ether (15 mL), and the suspension was heated with refluxing for 14 hours. After cooling the resultant mixture to a room temperature, diethyl ether was removed off, and toluene (20 mL) was added to the residue and successively the mixture was heated with refluxing for 10 minutes. After cooling to a room temperature, toluene was removed off, isopropyl ether was added to the residue and the mixture was heated with refluxing for 25 minutes. After cooling to a room temperature, isopropyl ether was removed off and toluene (20 mL) was added to the residue and successively the mixture was heated with refluxing for 35 minutes. After cooling to a room temperature, the precipitated solid was filtrated and washed with diethyl ether. After drying at 80° C. under a reduced pressure, the title compound (0.218 g) was obtained. The data of X-ray powder diffraction is shown in Table 4, and the chart of X-ray powder diffraction is shown in FIG. 4.

Elemental Analysis
Calculated (as $C_{16}H_{13}N_3O_2SF_3K.0.75H_2O$): C, 45.65; H, 3.47; N, 9.98. Found: C, 45.83; H, 3.71; N, 9.97.

K content by atomic absorption spectrometry: 9.0% (Calculated: 9.29%)

$^1$H-NMR (DMSO-$d_6$): 2.23 (3H, s), 4.42 (1H, d, J=12.8 Hz), 4.82–4.95 (3H, m), 6.85–6.91 (2H, m), 7.06 (1H, d, J=5.4 Hz), 7.43–7.48 (2H, m), 8.35 (1H, d, J=5.4 Hz)

TABLE 4

| 2θ (°) | half-value width | d-value [Å] | relative intensity [%] |
|---|---|---|---|
| 5.400 | 0.118 | 16.3519 | 100 |
| 10.820 | 0.165 | 8.1700 | 21 |

TABLE 4-continued

| 2θ (°) | half-value width | d-value [Å] | relative intensity [%] |
|---|---|---|---|
| 12.980 | 0.165 | 6.8148 | 18 |
| 15.320 | 0.165 | 5.7788 | 32 |
| 17.980 | 0.165 | 4.9294 | 17 |
| 19.720 | 0.165 | 4.4982 | 36 |
| 20.880 | 0.141 | 4.2509 | 26 |
| 21.760 | 0.188 | 4.0809 | 21 |
| 24.380 | 0.212 | 3.6480 | 19 |
| 26.480 | 0.141 | 3.3632 | 24 |
| 29.520 | 0.118 | 3.0234 | 18 |

Experimental Example 1

The crystal of a sodium salt obtained in Example 1 (about 5 mg) was served into a colorless glass bottle, the bottle was hermetically sealed by a stopper, and stability of the crystal during storage at 60° C. for 4 weeks was examined. 25 ml of a sample (concentration: about 0.2 mg/ml) was prepared by dissolving the sample after completion of storage in a mobile phase. The sample solution along with a standard solution prepared by using the initial lot (a frozen sample stored for the same term), was analyzed under the HPLC conditions shown below, and the content (residual percentage) was calculated from the peak area obtained.

[HPLC analytical Conditions]

Detection wavelength: UV 275 nm

Column: YMC Pro C18, 4.6ϕ 150 mm

Mobile phase: Fluid prepared by adding phosphoric acid to water/acetonitrile/triethylamine (63:37:1) to adjust pH 7

Flow rate: 1.0 mL/min

Column temperature: 40° C.

Sample injection volume: 10 μL

TABLE 5

| sample | storage condition | description | content [%] |
|---|---|---|---|
| crystal of Ex. 1 | freeze-storage | nearly white | [100] |
| crystal of Ex. 1 | 60° C. (airtight) for 4 weeks | nearly white | 99.2 |

As apparent from Table 5, when the sample was stored at 60° C. (airtight) for 4 weeks, the crystal retained a content exceeding 99%. This finding demonstrates that the crystal of a sodium salt of R(+)-lansoprazole is stable and suitable for use as a pharmaceutical etc.

Manufacturing Example 1

Among the following ingredients, sodium salt of Example 1, magnesium carbonate, saccharose, corn starch and crystalline cellulose were thoroughly mixed together to obtain a dusting powder. Nonpareils were put on a centrifugal fluidized coating granulator (CF-360, manufactured by Freund Inc.) and then the dusting powder was coated while spraying a hydroxypropyl cellulose solution (4%:W/V) to give spherical granules. The spherical granules were dried in vacuum at 40° C. for 16 hours and then passed through round sieve to give 12 to 32-mesh granules.

[Formulation in 190 mg of Granules]

| | |
|---|---|
| nonpareil | 75 mg |
| sodium salt of Example 1 | 15 mg |
| magnesium carbonate | 15 mg |
| saccharose | 29 mg |
| corn starch | 27 mg |
| crystalline cellulose | 27 mg |
| hydroxypropyl cellulose | 2 mg |
| water | (0.05 ml) |
| total | 190 mg |

Manufacturing Example 2

Enteric granules were produced by coating the granules obtained in Manufacturing Example 1 with an enteric coating agent having a formation shown below by means of a fluidized bed granulator (manufactured by Okawara) under conditions such that the inlet air temperature was 50° C. and the granule temperature was 40° C. The no. 2 hard capsule was filled with the enteric granules thus obtained in an amount of 240 mg per capsule using a capsule filling machine (manufactured by Parke-Davis).

[Formulation of Enteric Coating Agent]

| | |
|---|---|
| Eudragit L-30D | 104.7 mg |
| | (solids 31.4 mg) |
| Talc | 9.6 mg |
| Polyethylene glycol 6000 | 3.2 mg |
| Tween 80 | 1.6 mg |
| Titanium oxide | 4.2 mg |
| Water | (220 μl) |

[Formulation of enteric granules]

| | |
|---|---|
| Granules of Manufacturing Example 1 | 190 mg |
| Enteric coat | 50 mg |
| Total | 240 mg |

[Formulation of capsule]

| | |
|---|---|
| Enteric granules | 240 mg |
| No. 2 hard capsule | 65 mg |
| Total | 305 mg |

The invention claimed is:

1. A crystalline sodium salt, a crystalline lithium salt, a crystalline potassium salt, a crystalline magnesium salt, a crystalline calcium salt or a crystalline barium salt of (R)-2-[[[3-methyl-4-(2,2,2-trifluoroethoxy)-2-pyridinyl]methyl]sulfinyl]-1H-benzimidazole.

2. A salt according to claim 1, wherein said salt is a solvate with a water or an alcohol, or a non-solvate.

3. A salt according to claim 1, which is a crystalline sodium salt of (R)-2-[[[3-methyl-4-(2,2,2-trifluoroethoxy)-2-pyridinyl]methyl]sulfinyl]-1H-benzimidazole.

4. A salt according to claim 1, which is a crystalline potassium salt of (R)-2-[[[3-methyl-4-(2,2,2-trifluoroethoxy)-2-pyridinyl]methyl]sulfinyl]-1H-benzimidazole.

5. A pharmaceutical composition which comprises a salt recited in claim 1 and a pharmacologically acceptable carrier.

6. A method for treating digestive ulcer, ulcer caused by a nonsteroidal anti-inflammatory agent, or ulcer due to postoperative stress, which comprises administering an effective amount of salt recited in claim 1 to a human being in need thereof.

7. A crystalline sodium salt of (R)-2-[[[3-methyl-4-(2,2,2-trifluoroethoxy)-2-pyridinyl]methyl]sulfinyl]-1H-benzimidazole, said salt having an X-ray diffraction spectrum of the following diffraction peaks:
   (i) 15.02, 7.53, 7.05, 5.53, 4.17, 3.96, 3.42, 3.33 Å,
   (ii) 16.00, 12.65, 7.98, 7.51, 6.35, 5.09, 4.99, 4.92, 4.82, 4.21 Å, or
   (iii) 8.89, 8.47, 5.64, 5.24, 4.84, 4.23, 4.20, 4.09, 3.60, 3.36 Å.

8. A crystalline potassium salt of (R)-2-[[[3-methyl-4-(2,2,2-trifluoroethoxy)-2-pyridinyl]methyl]sulfinyl]-1H-benzimidazole, said salt having an X-ray diffraction spectrum of the following diffraction peaks:
   16.35, 8.17, 6.81, 5.78, 4.93, 4.50, 4.25, 4.08, 3.65, 3.36, 3.02 Å.

9. A process for producing a sodium salt of claim 7 comprising:
   reacting (R)-2-[[[3-methyl-4-(2,2,2-trifluoroethoxy)-2-pyridinyl]methyl]sulfinyl]-1H-benzimidazole with a compound of a sodium metal, and
   subjecting the sodium salt of (R)-2-[[[3-methyl-4-(2,2,2-trifluoroethoxy)-2-pyridinyl]methyl]sulfinyl]-1H-benzimidazole to crystallization to produce a sodium salt of claim 7.

10. A process for producing the potassium salt of claim 8 comprising:
    reacting (R)-2-[[[3-methyl-4-(2,2,2-trifluoroethoxy)-2-pyridinyl]methyl]sulfinyl]-1H-benzimidazole with a compound of a potassium metal, and
    subjecting the potassium salt of (R)-2-[[[3-methyl-4-(2,2,2-trifluoroethoxy)-2-pyridinyl]methyl]sulfinyl]-1H-benzimidazole to crystallization to produce the potassium salt of claim 8.

* * * * *

UNITED STATES PATENT AND TRADEMARK OFFICE
CERTIFICATE OF CORRECTION

PATENT NO. : 7,271,182 B2
APPLICATION NO. : 10/343142
DATED : September 18, 2007
INVENTOR(S) : Kamiyama et al.

It is certified that error appears in the above-identified patent and that said Letters Patent is hereby corrected as shown below:

Title page, (56) Reference Cited, line 15 of the second column (Other Publications): "Gastroeneterology" should read --Gastroenterology--.
Column 1, line 31: "pyridylmethylsulfiniyl" should read --pyridylmethylsulfinyl--.
Column 4, line 50: "nitrites" should read --nitriles--.
Column 5, line 24: "-0.1 mol" should read --0.1 mol--.
Column 5, line 38: "nitrites" should read --nitriles--.
Column 6, line 23: "nitrites" should read --nitriles--.
Column 9, line 62: "a-crystalline" should read --a crystalline--.
Column 16, line 4: "$C_{16}H_{13}N_3O_2SF_3Na.C_3H_8O.1.5H_2O$" should read --$C_{16}H_{13}N_3O_2SF_3Na·C_3H_8O·1.5H_2O$--.
Column 16, line 29: "Monohydrate" should read --monohydrate--.
Column 16, line 54: "$C_{16}H_{13}N_3O_2SF_3Na.H_2O$" should read --$C_{16}H_{13}N_3O_2SF_3Na·H_2O$--.
Column 17, line 46: "$C_{32}H_{26}N_6O_4S_2F_6Mg.4.5H_2O$" should read --$C_{32}H_{26}N_6O_4S_2F_6Mg·4.5 H_2O$--.
Column 18, line 2: "$C_{32}H_{26}N_6O_4S_2F_6Mg.1.5CH_3OH.2.5H_2O$" should read --$C_{32}H_{26}N_6O_4S_2F_6Mg·1.5CH_3OH·2.5H_2O$--.
Column 18, line 52: "$C_{16}H_{13}N_3O_2SF_3K.0.75H_2O$" should read --$C_{16}H_{13}N_3O_2SF_3K·0.75H_2O$--.

Signed and Sealed this

Twenty-first Day of October, 2008

JON W. DUDAS
*Director of the United States Patent and Trademark Office*